US012685756B2

(12) United States Patent
Markham et al.

(10) Patent No.: US 12,685,756 B2
(45) Date of Patent: Jul. 21, 2026

(54) METHODS OF TREATING DISEASE WITH TERLIPRESSIN

(71) Applicant: BIOVIE INC., Reno, NV (US)

(72) Inventors: Penelope Markham, Clifton, VA (US);
Joseph M. Palumbo, Saint Davids, PA (US)

(73) Assignee: BIOVIE INC., Reno, NV (US)

( * ) Notice: Subject to any disclaimer, the term of this patent is extended or adjusted under 35 U.S.C. 154(b) by 0 days.

(21) Appl. No.: 18/105,293

(22) Filed: Feb. 3, 2023

(65) Prior Publication Data

US 2023/0241156 A1     Aug. 3, 2023

Related U.S. Application Data

(60) Provisional application No. 63/306,368, filed on Feb. 3, 2022.

(51) Int. Cl.
| | |
|---|---|
| A61K 38/095 | (2019.01) |
| A61B 5/145 | (2006.01) |
| A61K 9/00 | (2006.01) |

(52) U.S. Cl.
CPC .......... A61K 38/095 (2019.01); A61K 9/0019 (2013.01); A61B 5/14546 (2013.01)

(58) Field of Classification Search
CPC . A61K 38/095; A61K 9/0019; A61B 5/14546
See application file for complete search history.

(56) References Cited

FOREIGN PATENT DOCUMENTS

| WO | WO-2017004317 A1 * | 1/2017 | ................ A61P 1/00 |
| WO | 2020160398 A1 | 8/2020 | |

OTHER PUBLICATIONS

Moore et al. (JAMA Clinical Evidence Synopsis, 2018, vol. 319, No. 8).*
Prakaso et al. (Intern Med J. Mar. 2013;43(3):240-6).*
Filippatos et al. (Clinical Interventions in Aging 2017:12 1957-1965).*
Prakaso et al. (Intern Med J. Mar. 2013;43(3):240-6. (Year: 2013).*
Filippatos et al. (Clinical Interventions in Aging 2017:12 1957-1965) (Year: 2017).*
Moore et al. (JAMA Clinical Evidence Synopsis, 2018, vol. 319, No. 8) (Year: 2018).*
International Search Report and Written Opinion for related International Application No. PCT/US23/12258, dated Apr. 18, 2023.
Liamis, G. "Hyponatremia-Inducing Drugs" 167-177. Disorders of Fluid and Electrolyte Metabolism. Focus on Hypo on Hyponatremia, Front Horm Res. Basel, Karger, 2019, 2019, vol. 52, pp. 167-177, DOI: 10.1159/000493246.
Lu, X. (2016) "Hyponatremia induced by antiepileptic drugs in patients with epilepsy" 1-40. Expert Opinion on Drug Safety, DOI: 10.1080/14740338.2017.1248399.

Eriksen, et al.; Terlipressin for variceal bleeding induces large plasma sodium fluctuations in patients without cirrhosis. United European Gastroenterol J. Oct. 2018; 6(8):1199-1205.
Escorsell, et al; Time profile of the haemodynamic effects of terlipressin in portal hypertension. J. Hepatol. Mar. 1997; 26(3):621-7.
Falhammar, et al.; Differences in associations of antiepileptic drugs and hospitalization due to hyponatremia: A population-based case-control study. Seizure. Jul. 2018; 59:28-33.
Kang, et al; Initial serum sodium concentration determines the decrease in sodium level after terlipressin administration in patients with liver cirrhosis. Springerplus. 2013; 2:519.
Krag, et al.; Effects of terlipressin on the aquaretic system: evidence of antidiuretic effects. Am. J. Physiol. Renal Physiol. Nov. 2008; 295(5):F1295-300.
McClure, et al.; Long-term continuous terlipressin infusion in cirrhotic patients with hepatorenal syndrome or refractory ascites awaiting liver transplantation is associated with an increase in plasma sodium. United European Gastroenterol. J. Nov. 2019; 7(9):1271-1273.
Ortega, et al.; Terlipressin therapy with and without albumin for patients with hepatorenal syndrome: results of a prospective, nonrandomized study. Hepatology. Oct. 2002; 36(4 Pt 1):941-8.
Solà, et al.; Hyponatremia in patients treated with terlipressin for severe gastrointestinal bleeding due to portal hypertension. Hepatology. Nov. 2010; 52(5):1783-90.
Wong, et al.; CONFIRM Study Investigators. Terlipressin plus Albumin for the Treatment of Type 1 Hepatorenal Syndrome. N. Engl. J. Med. Mar. 4, 2021; 384(9):818-828.
Youn Joo Jung et al., A Case Report of Syndrome of Inappropriate Antidiuretic Hormone Induced by Pregabalin. Electrolyte Blood Press. 2016, 14:31-34.
Bernardi and Zaccherini (2018). Approach and management of dysnatremias in cirrhosis. Hepat. Int. 12(6): 487-499.
Fagundes and Ginès (2012). Hepatorenal syndrome: a severe, but treatable, cause of kidney failure in cirrhosis. Am. J. Kidney Dis. 59(6): 874-885.
Fimiani et al. (2011). The use of terlipressin in cirrhotic patients with refractory ascites and normal renal function: a multicentric study. Eur. J. of Intern. Med. 22(6): 587-590.

(Continued)

*Primary Examiner* — Tara L Martinez
(74) *Attorney, Agent, or Firm* — McDonnell Boehnen Hulbert & Berghoff LLP

(57) ABSTRACT

Provided are methods of treating a disease with arginine vasopressin or an analogue thereof that reduce the risk of hyponatremia. Specifically, the invention relates to the novel observation that subjects receiving co-administration of terlipressin and gabapentin or pregabalin have a high incidence of severe hyponatremia. The methods of the invention include either excluding subjects receiving gabapentin, gabapentin analogues, gabapentinoids, and other drugs known to cause hyponatremia from treatment with arginine vasopressin or analogues thereof; or reducing the subject's dose of gabapentin, gabapentin analogues, gabapentinoids, and other drugs known to cause hyponatremia prior to administration with arginine vasopressin or analogues thereof; or discontinuing administration of gabapentin, gabapentin analogues, gabapentinoids, and other drugs known to cause hyponatremia during the course of administration of arginine vasopressin or analogues thereof or reducing the dose of the arginine vasopressin or analogues thereof.

19 Claims, 4 Drawing Sheets

(56) References Cited

OTHER PUBLICATIONS

Subba et al. (2023). "Vasopressin-Induced Hyponatremia in Patients With Aneurysmal Subarachnoid Hemorrhage: A Case Series and Literature Review." J. Pharm. Pract. 36(3): 689-694. Note: first published online Oct. 21, 2021 according to publisher website: <https://doi.org/10.1177/08971900211053497>.

\* cited by examiner

FIG. 1

|  | Baseline | D2 | D3 | D4 | D5 | D7 | D14 | D21 | D+2 | D+6 | D+10 | D+15 |
|---|---|---|---|---|---|---|---|---|---|---|---|---|
| Terlipressin acetate mg/day | - | 3 | 3 | 3 | 3 | 4 | ↓ 3 | STOP | 0 | 0 | 0 | 0 |
| Furosemide/ Spironolactone mg/day | 20/- | 20/- | 20/- | 20/- | 20/- | 20/- | STOP |  |  |  |  |  |
| Serum Na mmol/L | 139 | 138 |  |  |  | 136 | 128 | 124 | 131 | 134 | 135 | 138 |

FIG. 2

| | Baseline | D2 | D7 | D14 | D17 | D20 | D21 | D29 |
|---|---|---|---|---|---|---|---|---|
| Terlipressin acetate mg/day | - | 3 | 3 | Interrupted | 2 | 3 | 3 | STOP |
| Furosemide/ Spironolactone mg/day | 0/0 | 0/0 | 0/0 | 0/0 | 0/0 | 0/0 | 0/0 | |
| Serum Na mmol/L | 137 | 131 | 123 | 124/127 | 134 | 133 | 134 | 127 |

FIG. 3

| | Baseline | D1 | D6 | D14 | D16 | D20 | D28 | D+1 | D+2 | D+3 | D+10 |
|---|---|---|---|---|---|---|---|---|---|---|---|
| Terlipressin acetate mg/day | - | 3 | 3 | 4 | 4 | 4 | STOP | 0 | 0 | 0 | 0 |
| Furosemide/ Spironolactone mg/day | 40/200 | 40/200 | 40/200 | 40/200 | 40/200 | 40/200 | 40/200 | 40/200 | 40/200 | 40/200 | 40/200 |
| Serum Na mmol/L | | 129 | 133 | 132 | 129 | 129 | 119 | 117/119 | 120 | 121/125 | 126 |

FIG. 4

| | Baseline | D2 | D3 | D4 | D5 | D6 | D7 | D8 | D9 | D10 | D+1 | D+2 | D+3 | D+15 |
|---|---|---|---|---|---|---|---|---|---|---|---|---|---|---|
| Terlipressin acetate mg/day | 0 | 2 | 2 | 2 | 3 | 3 | 3 | 2 | 2 | 2 | 0 | 0 | 0 | 0 |
| Furosemide/Spironolactone mg/day | 20/100 | 20/100 | 20/100 | 20/100 | 20/100 | 0/100 | 0/100 | 0/100 | 0 | 0 | 0 | 0 | 0 | 0 |
| Serum Na mmol/L | 139 | 138 | 137 | 132 | 128 | 128 | 126 | 126 | 125 | 124 | 124 | 130 | 135 | 138 |

METHODS OF TREATING DISEASE WITH TERLIPRESSIN

CROSS REFERENCE TO RELATED APPLICATIONS

The present application claims priority to U.S. Provisional Application No. 63/306,368, filed Feb. 3, 2022, the entirety of which is incorporated herein by reference.

BACKGROUND

Terlipressin is considered a pro-drug of its more potent metabolite 8-lysine vasopressin (8-LVP), an analogue of human nonapeptide hormone arginine vasopressin (AVP). Terlipressin differs from AVP in the addition of three glycyl residues at the amino terminus and the substitution of lysine for arginine at the eighth position. After intravenous administration the terminal glycine residues are sequentially removed to yield 8-LVP. Terlipressin mediates its vasoconstrictive activity via high affinity binding of 8-LVP to vasopressin Type 1 receptors which are located, in high density, on vascular smooth muscle of the systemic, splanchnic, renal, and coronary circulations and also on myometrium and platelets. Both AVP and 8-LVP bind vasopressin type 2 receptors in the kidney and cause antidiuretic effects by stimulating reabsorption of water through aquaporin channels. The binding affinity of 8-LVP for vasopressin type 2 receptors is approximately 12 fold less than AVP. The AVP analogue desmopressin, used long-term on an outpatient basis to treat nocturia, binds selectively to V2 type receptors and has anti-diuretic activity but does not possess vasoconstrictive activity. Oxytocin, a nonapeptide differing from AVP by only two amino acids, also binds V2 receptors and causes antidiuretic activity.

Terlipressin is approved outside of the United States for the treatment of two life-threatening complications of cirrhosis—namely hepatorenal syndrome type 1 (HRS-1) or more recently called HRS-acute kidney injury (HRS-AKI) and bleeding esophageal varices (called BEV or EVB).

Vasopressin and its analogues that activate V2 receptors cause antidiuretic effects and water retention with the risk of reducing serum sodium or hyponatremia. The incidence of desmopressin-induced hyponatremia is reportedly 7.6% in adults with nocturia (*Neurourol. Urodyn.* 23, 302-305. doi: 10.1002/nau.20038). It has been documented that terlipressin, administered acutely as a single bolus dose, mediates antidiuretic effects (Krag, 2008) which can potentially lead to water retention, hypervolemia, dilution of serum sodium concentrations and hyponatremia (dilutional hyponatremia). Indeed, in the acute treatment setting for BEV (terlipressin bolus injections of 2 mg administered up to 4 times a day for up to 2 days), 67% of patients with portal hypertensive bleeding treated with terlipressin experienced hyponatremia defined as ≥5 mmol decrease in serum sodium (Sola, 2010). However, the incidence of hyponatremia in BEV patients with advanced cirrhosis treated with terlipressin is likely far lower since the incidence of severe hyponatremia (≥10 mmol/L reduction in serum sodium) increases greatly (27% vs 4%) in patients with non-cirrhotic portal hypertension vs those with portal hypertension due to cirrhosis (Eriksen 2018).

The incidence of hyponatremia is reportedly far lower in cirrhotic patients treated longer-term for hepatorenal syndrome type 1 vs BEV (14% versus 41%, Kang 2013). It has been reported that terlipressin, administered over 14 days in conjunction with daily albumin to HRS patients, can even correct low serum sodium (Ortega, 2002). The largest and most recently conducted randomized placebo-controlled trial of terlipressin administered by intermittent bolus injections for up to 14 days for the treatment of hepatorenal syndrome reported <5% incidence of hyponatremia in 199 patients treated with terlipressin (Wong, 2021 supplemental data Table S9a).

The incidence of hyponatremia in cirrhotic patients treated long-term with terlipressin administered as a continuous infusion is anticipated to be even less frequent. Administration of terlipressin as a continuous infusion versus repeated IV bolus dosing can minimize the potential for antidiuretic effects of terlipressin and the development of hyponatremia in this patient population. With bolus IV administration the V1-mediated pharmacodynamic effects of terlipressin last 3-4 hours where V2 mediated antidiuretic effects can predominate in hours 4-6 between bolus doses (Escorsell 1997). Administering terlipressin as a continuous infusion versus bolus dosing can minimize the risk of V2-mediated antidiuretic effects by maintaining a steady plasma concentration where V1 effects are maintained outweighing V2 effects, thus reducing the risk of hyponatremia.

Indeed it has been reported that longer term treatment of cirrhotic patients with recurrent HRS or refractory ascites, with terlipressin administered as a continuous infusion in the outpatient setting without daily albumin, can not only improve renal function and reduce ascites but also improve serum sodium concentrations (McGlure 2019).

There is increasing interest in using terlipressin long-term, including on an outpatient basis, to treat or prevent complications of cirrhosis including hyponatremia, adrenal insufficiency, recurrent hepatorenal syndrome and/or ascites. With more limited monitoring in the outpatient setting it is imperative to reduce the risk of hyponatremia associated with use of terlipressin since hyponatremia is associated with hepatic encephalopathy and can increase the risk of seizures and even death. Likewise, in a more acute care setting, including the treatment of hepatorenal syndrome, bleeding varices and hypotension, it is important to minimize the risk of severe hyponatremia (reduction in serum sodium of >10 mmol/L), which has been reported to occur in more than 12% of patients, at least 30% of whom experience neurological manifestations. In this setting a reduction in serum sodium can occur rapidly with the majority of patients experiencing the reduction in serum sodium by the third day of treatment [Kang 2013]. Accordingly, there is a need for methods to predict and reduce the risk of hyponatremia in patients receiving terlipressin, vasopressin, analogues of vasopressin or related peptides with V2 receptor activity, particularly in the outpatient setting where patients are monitored less frequently.

SUMMARY

The present disclosure is directed to a method of administering arginine vasopressin or an analogue thereof to a subject, the method comprising assessing whether the subject is receiving one or more drugs selected from the group gabapentin, gabapentin analogues, gabapentinoids, and other drugs known to cause hyponatremia; and administering the arginine vasopressin or analogue thereof to the subject only if the subject is not receiving the one or more drugs.

The present disclosure is also directed to a method of administering arginine vasopressin or an analogue thereof to a subject, the method comprising assessing whether the subject is receiving one or more drugs selected from the group gabapentin, gabapentin analogues, gabapentinoids, and other drugs known to cause hyponatremia; reducing the subject's dose of the one or more drugs; and administering the arginine vasopressin or analogue thereof to the subject only once the subject's dose of the one or more drugs has been reduced.

The present disclosure is also directed to a method of reducing the risk of hyponatremia in a subject receiving arginine vasopressin or an analogue thereof, the method comprising assessing whether the subject is receiving one or more drugs selected from the group gabapentin, gabapentin analogues, gabapentinoids, and other drugs known to cause hyponatremia; stopping administration or reducing the dose of the arginine vasopressin or analogue thereof to the subject if the subject is receiving the one or more drugs; and resuming administration of the arginine vasopressin or analogue thereof at the original dose to the subject once the subject has been weaned off or weaned to a reduced dose of the one or more drugs.

In any of the foregoing embodiments, the one or more drugs is gabapentin or pregabalin.

In any of the foregoing embodiments, administering arginine vasopressin or an analogue thereof comprises continuous infusion, IV injection bolus, IV injection slow bolus, subcutaneous administration by injection or infusion or intranasal delivery.

The present disclosure is also directed to a method comprising administering to a subject a therapeutically effective amount of arginine vasopressin or an analogue thereof and monitoring the subject's serum sodium levels for hyponatremia.

BRIEF DESCRIPTION OF THE DRAWINGS

For the purpose of illustrating the disclosure, there are depicted in the drawings certain embodiments of the disclosure. However, the disclosure is not limited to the precise arrangements and instrumentalities of the embodiments depicted in the drawings.

FIG. 1 depicts daily terlipressin dose, diuretic dose(s), and serum sodium levels of Patient #1 before and after initiation of treatment with terlipressin administered as a continuous infusion.

FIG. 2 depicts daily terlipressin dose, diuretic dose(s), and serum sodium levels of Patient #2 before and after initiation of treatment with terlipressin administered as a continuous infusion.

FIG. 3 depicts daily terlipressin dose, diuretic dose(s), and serum sodium levels of Patient #3 before and after initiation of treatment with terlipressin administered as a continuous infusion.

FIG. 4 depicts daily terlipressin dose, diuretic dose(s), and serum sodium levels of Patient #4 before and after initiation of treatment with terlipressin administered as a continuous infusion.

DETAILED DESCRIPTION

The current invention is directed to a novel method of administering arginine vasopressin or an analogue thereof. Those of skill in the art will appreciate the various analogues of arginine vasopressin. By way of example but not limitation, analogues of arginine vasopressin include terlipressin, argipressin, desmopressin, felypressin, lypressin, or ornipressin. The method comprises administering arginine vasopressin or an analogue thereof only to subjects that are not concurrently receiving gabapentin, analogues of gabapentin, gabapentinoids, or other drugs known to cause hyponatremia, or alternatively administering arginine vasopressin or an analogue thereof only to subjects on reduced doses of gabapentin, analogues of gabapentin, gabapentinoids, or other drugs known to cause hyponatremia, thereby reducing the risk of hyponatremia in subjects receiving arginine vasopressin or an analogue thereof.

Another embodiment of the invention comprises a method of reducing the risk of hyponatremia in a subject receiving arginine vasopressin or an analogue thereof, by assessing whether the subject is receiving one or more drugs selected from the group gabapentin, gabapentin analogues, gabapentinoids, and other drugs known to cause hyponatremia; reducing the dose of the arginine vasopressin or analogue thereof or stopping administration of the arginine vasopressin or analogue thereof to the subject if the subject is receiving the one or more drugs; and resuming administration of the arginine vasopressin or analogue thereof to the subject at the previous dose or a lower dose only once the subject has been weaned off the one or more drugs or their dose of one or more drugs has been reduced.

Gabapentin, an anti-convulsant approved in the US in the mid-1990s, has become increasingly used off label to treat neuropathic pain. Indeed, in 2019 gabapentin was reported to be the seventh most commonly prescribed medication in the US (Mattson C L, Chowdhury F, Gilson T P. *Notes from the Field*: Trends in Gabapentin Detection and Involvement in Drug Overdose Deaths—23 States and the District of Columbia, 2019-2020. MMWR Morb Mortal Wkly Rep 2022; 71:664-666; http://dx.doi.org/10.15585/mmwr.mm7119a3external icon). The off-label prescribing of gabapentin to cirrhotic patients has increased more recently due to its appreciated efficacy in managing neuropathic pain associated with diabetes and the increasing proportion of cirrhotic patients whose disease is caused by non-alcoholic steatohepatitis disease who have concomitant diabetes and thus diabetes-associated neuropathic pain. Since it is not metabolized by the liver and not protein bound it is recommended, in patients with cirrhosis, as a first-line anti-epileptic (Pediatr Neurol. 2017 December; 77:23-36; doi: 10.1016/j.pediatrneurol.2017.09.013) and to consider gabapentin as first line nonopioid therapy, particularly for patients with neuropathic pain (Rakoski et al., Pain management in patients with cirrhosis, Clinical Liver Disease, 11:6, 135-140 (June 2018); https://doi.org/10.1002/cld.711). Though not a substantially addictive substance, completely discontinuing treatment of gabapentin can cause withdrawal symptoms such as confusion, disorientation, gastrointestinal issues, sweating, hypertension, insomnia, and seizures. For these reasons, it is recommended that subjects gradually decrease the dose of gabapentin before discontinuing use.

The current invention is based on the surprising observation that gabapentin, an anti-convulsant with no reported connection to anti-diuresis/vasopressin/V2 receptors/aquaporin, that is not included in lists of drugs that may cause hyponatremia (drug-induced-hyponatraemia.pdf (resourcepharm.com) and with the lowest risk of hyponatremia among anti-epilepsy drugs (Falhammar 2018)—may increase the risk of hyponatremia in cirrhotic patients being treated with terlipressin. This association may have gone unnoticed in earlier studies with terlipressin as recommendations for the use of gabapentinoids in cirrhotic patients have been made only recently.

In some embodiments, the risk of developing hyponatremia is reduced by treating subjects with arginine vasopressin or an analogue thereof only if that subject is not concurrently receiving gabapentin, analogues of gabapentin, gabapentinoids such as pregabalin, or other drugs known to cause hyponatremia such as arbamazepine, oxcarbazepine, eslicarbazepine, sodium valproate, lamotrigine, and levetiracetam.

In some embodiments, the administration of arginine vasopressin or an analogue thereof is discontinued, interrupted or the dose reduced in a subject already receiving arginine vasopressin or an analogue thereof if it is revealed that the subject is also receiving gabapentin, analogues of gabapentin, gabapentinoids such as pregabalin, or other drugs known to cause hyponatremia such as arbamazepine, oxcarbazepine, eslicarbazepine, sodium valproate, lamotrigine, and levetiracetam. The administration of arginine vasopressin or an analogue thereof is only continued when the subject has been weaned off or weaned to a reduced dose of the gabapentin, analogues of gabapentin, gabapentinoids such as pregabalin, or other drugs known to cause hyponatremia such as arbamazepine, oxcarbazepine, eslicarbazepine, sodium valproate, lamotrigine, and levetiracetam.

In any of the foregoing embodiments, arginine vasopressin or an analogue thereof administration may comprise continuous or bolus administration. By way of non-limiting example, to treat BEV an i.v. injection bolus of 2 mg terlipressin initially is given to a subject every 4 hours. When the bleeding is under control the dose can be adjusted to 1 mg terlipressin acetate i.v. every 4 hours. The treatment should not continue for more than 48 hours in total. Another non-limiting example of terlipressin administration, to treat HRS-1, a subject may receive bolus injection of 1-2 mg of terlipressin every 6 hours for up to 14 days.

The frequency of the dose is readily apparent to the skilled artisan and depends upon any number of factors, such as, but not limited to, the type and severity of the disease being treated. Actual dosage levels of the arginine vasopressin or analogue thereof of this disclosure may be varied so as to obtain an amount of the active ingredient that is effective to achieve the desired therapeutic response for a particular patient, composition, and mode of administration, without being toxic to the patient. A medical doctor, e.g., physician or veterinarian, having ordinary skill in the art may readily determine and prescribe the effective amount of the pharmaceutical composition required.

Administration of arginine vasopressin or an analogue thereof to a subject, preferably a mammal, more preferably a human, may be carried out using known procedures, at dosages and for periods of time effective to treat or prevent BEV, HRS-1 or to reduce ascites in the subject. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation.

The present disclosure provides administration of arginine vasopressin or an analogue thereof as a continuous infusion, IV injection bolus, slow bolus or subcutaneous injection or infusion. With bolus IV administration the V1-mediated pharmacodynamic effects of terlipressin last 3-4 hours where V2 mediated antidiuretic effects can predominate in hours 4-6 between bolus doses. Administering arginine vasopressin or an analogue thereof as a continuous infusion versus bolus dosing can minimize the risk of V2-mediated antidiuretic effects by maintaining a steady plasma concentration where V1 effects are maintained outweighing V2 effects.

EXAMPLES

The disclosure is described with reference to the following Examples. These Examples are provided for the purpose of illustration only and the disclosure should in no way be construed as being limited to these Examples, but rather should be construed to encompass any and all variations which become evident as a result of the disclosure provided herein.

Without further description, it is believed that one of ordinary skill in the art can, using the preceding description and the following illustrative examples, practice the claimed methods. The following working examples are not to be construed as limiting in any way the present disclosure.

Example 1: Clinical Observation of Hyponatremia in Patients Treated with Terlipressin The following clinical observations were made in an ongoing clinical trial evaluating the safety and efficacy of terlipressin, administered as a continuous infusion, in patients with cirrhosis and refractory ascites. In FIGS. 1-4, "D" stands for "Day" and the notation "Dn" where n is an integer refers to the number of days after the baseline sodium level was measured. The notation "D+N" where N is an integer refers to the number of days after administration of terlipressin was stopped.

Patient #1, a 65 year old female patient with cirrhosis due to NASH and recurrent ascites that was not responding to treatment with the diuretic furosemide initiated infusion with terlipressin (3 mg/day) on Day 1. Terlipressin dose (mg/day), furosemide daily dose, and serum sodium levels of the Patient #1 are recorded in FIG. 1. After 6 days of treatment with terlipressin at a dose of 3 mg/day the dose of terlipressin was escalated to 4 mg/day as per protocol. A modest reduction in serum sodium of 3 mmol/L from baseline was noted before the dose increase. After 7 days of treatment with 4 mg/day serum sodium decreased an additional 8 mmol/L so that there was a total reduction of 11 mmol/L in the 13 days of treatment versus baseline (128 vs 139 mmol/L). The diuretic furosemide was discontinued for 7 days and serum sodium continued to decrease by an additional 4 mmol/L to 124 mmol/L. The patient was asymptomatic. Terlipressin infusion was discontinued. Two days later serum sodium had increased by 7 mmol/L to 131 mmol/L and continued to gradually increase to 135 mmol/L 10 days after discontinuation. The hyponatremia was considered related to terlipressin.

Patient #2, a 63 year old male with alcoholic cirrhosis and recurrent ascites who could not be treated with diuretics began treatment with terlipressin at a dose of 3 mg/day. The daily terlipressin dose and serum sodium levels of the Patient #2 are recorded in FIG. 2. The following day serum sodium decreased from 137 mmol/L at baseline to 131 mmol/L and since the patient was asymptomatic treatment continued to Day 7 where serum sodium was noted to have reduced to 123 mmol/L. The patient remained asymptomatic and treatment continued to Day 14 and serum sodium remained at 124 mmol/L. Terlipressin infusion was interrupted and serum sodium rebounded to 134 mmol/L after 3 days. The hyponatremia was considered related to terlipressin.

Patient #3, a 52 year old male with cirrhosis due to NASH, with uncontrolled ascites despite ongoing treatment with the diuretics furosemide and spironolactone, initiated treatment with terlipressin administered as a continuous intravenous infusion at a dose of 3 mg/day. Terlipressin dose (mg/day), furosemide daily dose, and serum sodium levels of the Patient #3 are recorded in FIG. 3. After 14 days of treatment serum sodium decreased slightly from 134 mmol/L pre-treatment to 132 mmol/L. The terlipressin dose was increased to 4 mg/day and serum sodium was 129 mmol/L 2 days and 6 days later. Treatment continued and serum sodium was noted to have decreased to 117 mmol/L on Day 28 and infusion was stopped. Though the patient was asymptomatic the patient was directed to go to the Emergency room. Serum sodium gradually increased 10 mmol/L over the next 3 days to 127 mmol/L. The hyponatremia was considered related to terlipressin.

Patient #4, who was one of 6 patients treated with terlipressin administered as a continuous infusion in our previous Phase 2a trial, was a 63 year old male with recurrent ascites due to cirrhosis despite taking the antidiuretics spironolactone and furosemide. Terlipressin, furosemide, and serum sodium levels of Patient #3 are recorded in FIG. 4. According to protocol this patient began treatment with terlipressin at an initial dose of 2 mg/day who was escalated to a dose of 3 mg/day on Day 5. Serum sodium gradually declined over time reaching a reduction of 10 mmol/L on Day 5 at which point the patient stopped taking furosemide. Serum sodium continued to decline and spironolactone was stopped for two days which had no impact on declining serum sodium. Terlipressin infusion was stopped after 9 days of treatment and serum sodium rebounded after 2 days of drug cessation. The severe hyponatremia, which was asymptomatic, was considered related to terlipressin treatment.

Given the low incidence of hyponatremia expected with treating cirrhotic patients with terlipressin administered as a continuous infusion it was surprising that 3 of the 10 (30%) cirrhotic patients with ascites treated to date with terlipressin administered long-term as a continuous infusion developed hyponatremia, with a reduction in serum sodium of ≥10 mmol/L that was considered related to terlipressin (see examples below). Additionally, one patient in our previously conducted Phase 2a trial (n=6) similarly developed asymptomatic hyponatremia in response to terlipressin administration.

In searching for a commonality between the three patients that experienced hyponatremia in response to terlipressin treatment in the current trial it was noted that the three patients were taking daily gabapentin (Patient #1 and 2) or pregabalin (Patient #3) though none of the other 7 patients randomized to treatment with terlipressin were taking either of these medications. Moreover, the one patient out of six who developed hyponatremia in response to terlipressin in the previous Phase 2a trial was also taking gabapentin.

Example 2: Detecting Hyponatremia in an Outpatient Setting

Given the known association of arginine vasopressin or analogues thereof with hyponatremia it has previously been recommended to monitor serum sodium levels in patients being treated with arginine vasopressin or analogues thereof. Monitoring of patients being treated with drugs known to cause hyponatremia may include daily assessment for symptoms of hyponatremia such as confusion, nausea, vomiting, and mental status change; monitoring of serum sodium 1-2 days after dose initiation or dose escalation and weekly during the entire treatment cycle; and interrupting treatment if sNA goes below a specified threshold e.g., <125 mmol/L.

REFERENCES

Eriksen P L, Hartkopf-Mikkelsen A L, Ott P, Vilstrup H, Aagaard N K. Terlipressin for variceal bleeding induces large plasma sodium fluctuations in patients without cirrhosis. United European Gastroenterol J. 2018 October; 6(8):1199-1205.

Escorsell A, Bandi J C, Moitinho E, Feu F, Garcia-Pagan J C, Bosch J, Rodés J. Time profile of the haemodynamic effects of terlipressin in portal hypertension. J Hepatol. 1997 March; 26(3):621-7.

Falhammar H, Lindh J D, Calissendorff J, Farmand S, Skov J, Nathanson D, Mannheimer B. Differences in associations of antiepileptic drugs and hospitalization due to hyponatremia: A population-based case-control study. Seizure. 2018 July; 59:28-33.

Kang Y J, Bae E J, Hwang K, et al. Initial serum sodium concentration determines the decrease in sodium level after terlipressin administration in patients with liver cirrhosis. *Springerplus*. 2013; 2:519.

Krag A, Bendtsen F, Pedersen E B, Holstein-Rathlou N H, Møller S. Effects of terlipressin on the aquaretic system: evidence of antidiuretic effects. Am J Physiol Renal Physiol. 2008 November; 295(5):F1295-300.

McClure T, Chapman B, Hey P, Testro A, Gow P. Long-term continuous terlipressin infusion in cirrhotic patients with hepatorenal syndrome or refractory ascites awaiting liver transplantation is associated with an increase in plasma sodium. United European Gastroenterol J. 2019 November; 7(9):1271-1273.

Ortega R, Ginès P, Uriz J, Cárdenas A, Calahorra B, De Las Heras D, Guevara M, Bataller R, Jiménez W, Arroyo V, Rodés J. Terlipressin therapy with and without albumin for patients with hepatorenal syndrome: results of a prospective, nonrandomized study. Hepatology. 2002 October; 36(4 Pt 1):941-8.

Solà E, Lens S, Guevara M, Martin-Llahí M, Fagundes C, Pereira G, Pavesi M, Fernández J, González-Abraldes J, Escorsell A, Mas A, Bosch J, Arroyo V, Ginès P. Hyponatremia in patients treated with terlipressin for severe gastrointestinal bleeding due to portal hypertension. Hepatology. 2010 November; 52(5):1783-90

Wong F, Pappas S C, Curry M P, Reddy K R, Rubin R A, Porayko M K, Gonzalez S A, Mumtaz K, Lim N, Simonetto D A, Sharma P, Sanyal A J, Mayo M J, Frederick R T, Escalante S, Jamil K; CONFIRM Study Investigators. Terlipressin plus Albumin for the Treatment of Type 1 Hepatorenal Syndrome. N Engl J Med. 2021 Mar. 4; 384(9):818-828.

What is claimed is:

1. A method of administering terlipressin or a salt thereof to a subject receiving one or more drugs selected from the group consisting of gabapentin, gabapentin analogues, and gabapentinoids, the method comprising—reducing the subject's dose of the one or more drugs and administering the terlipressin or a salt thereof to the subject.

2. The method of claim 1, wherein the one or more drugs is selected from gabapentin or pregabalin.

3. The method of claim 1, wherein administering the terlipressin or a salt thereof comprises continuous infusion, IV injection bolus, IV injection slow bolus, subcutaneous administration by injection or intranasal delivery.

4. The method of claim 1, wherein the one or more drugs is gabapentin.

5. The method of claim 1, wherein the one or more drugs is pregabalin.

6. The method of claim 1, wherein administering the terlipressin or a salt thereof comprises continuous infusion.

7. The method of claim 1, wherein the subject has ascites.

8. The method of claim 1, wherein administering the terlipressin or a salt thereof to the subject occurs only once the subject's dose of the one or more drugs has been reduced.

9. The method of claim 1, wherein reducing the subject's dose of the one or more drugs comprises weaning the subject off the one or more drugs.

10. The method of claim 1, wherein reducing the subject's dose of the one or more drugs comprises stopping the administration of the one or more drugs.

11. The method of claim 1, wherein the terlipressin or a salt thereof is in the form of terlipressin acetate.

12. The method of claim 1, wherein the terlipressin or a salt thereof is administered in an outpatient setting.

13. The method of claim 1, wherein the terlipressin or a salt thereof is administered at a dose of about 2 mg/day to about 4 mg/day.

14. The method of claim 1, wherein the terlipressin or a salt thereof is administered at a dose of 1 to 2 mg every 4 to 6 hours for up to 14 days.

15. The method of claim 1, further comprising reducing the subject's risk of hyponatremia.

16. The method of claim 15, wherein the subject has hyponatremia if the subject has a serum sodium level<125 mmol/L.

17. The method of claim 15, wherein the subject has hyponatremia if the subject has a serum sodium level decrease of at least 10 mmol/L.

18. The method of claim 1, wherein the one or more drugs is used for managing neuropathic pain.

19. The method of claim 1, wherein the subject has cirrhosis.

* * * * *